United States Patent [19]

Niklas et al.

[11] 3,996,791
[45] Dec. 14, 1976

[54] ULTRASONIC TEST METHOD AND APPARATUS UTILIZING SCATTERED SIGNALS

[75] Inventors: Ludwig Niklas, Lovenich, Germany; Joseph L. Rose, Philadelphia, Pa.; Udo Schlengermann, Hurth-Hermulheim, Germany

[73] Assignee: Krautkramer-Branson, Incorporated, Stratford, Conn.

[22] Filed: Apr. 24, 1975

[21] Appl. No.: 571,076

[52] U.S. Cl. .................................................. 73/67.7
[51] Int. Cl.² ..................................... G01N 29/04
[58] Field of Search .......... 73/67.7, 67.8 R, 67.8 S, 73/67.9; 235/151.3; 324/77 B; 340/15.5 CC, 15.5 DP

[56] References Cited
UNITED STATES PATENTS

| | | | |
|---|---|---|---|
| 3,140,600 | 7/1964 | Howry | 73/67.7 |
| 3,299,694 | 1/1967 | Dickenson | 73/67.7 X |
| 3,332,278 | 7/1967 | Wood et al. | 73/67.7 |
| 3,515,990 | 6/1970 | Robertson | 324/77 R |
| 3,776,026 | 12/1973 | Adler | 73/67.7 |
| 3,857,052 | 12/1974 | Beller | 73/67.85 X |

OTHER PUBLICATIONS

P. S. Fuss et al., Making the Fast Fourier Transform Really Fast, Bell Laboratories Record, Feb. 1973, 324–377 B.

*Primary Examiner*—James J. Gill
*Assistant Examiner*—John P. Beauchamp
*Attorney, Agent, or Firm*—Ervin B. Steinberg; Philip J. Feig

[57] ABSTRACT

In a pulse-echo ultrasonic test arrangement the back reflected echo acoustic wave signal as well as the scattered longitudinal wave and scattered shear wave signals are utilized in an evaluation circuit for determining more accurately the characteristics of a defect in a workpiece. The evaluation circuit, most suitably, includes a digital computer which in a typical embodiment of the invention is programmed to provide by Fourier transforms the frequency amplitude spectrum and the frequency phase spectrum of the supplied three signals, hence producing six characteristic outputs for a particular defect.

15 Claims, 6 Drawing Figures

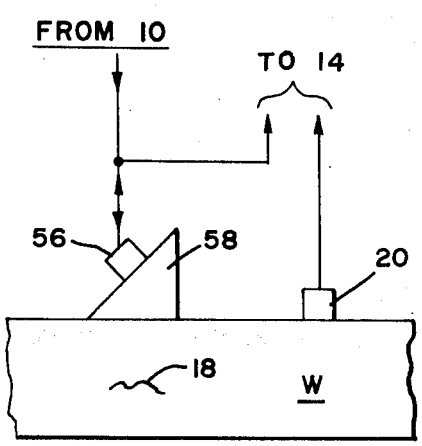
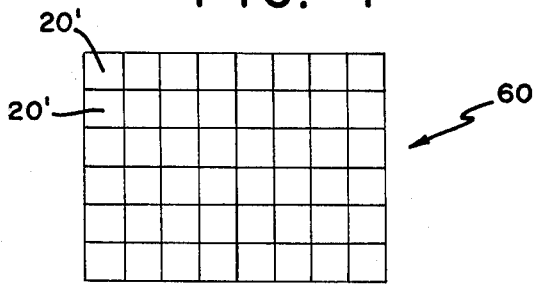
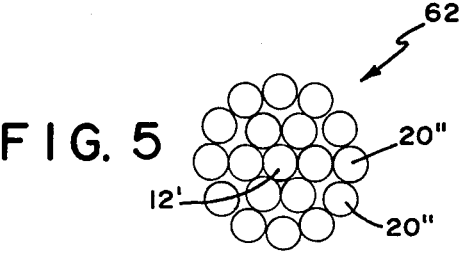
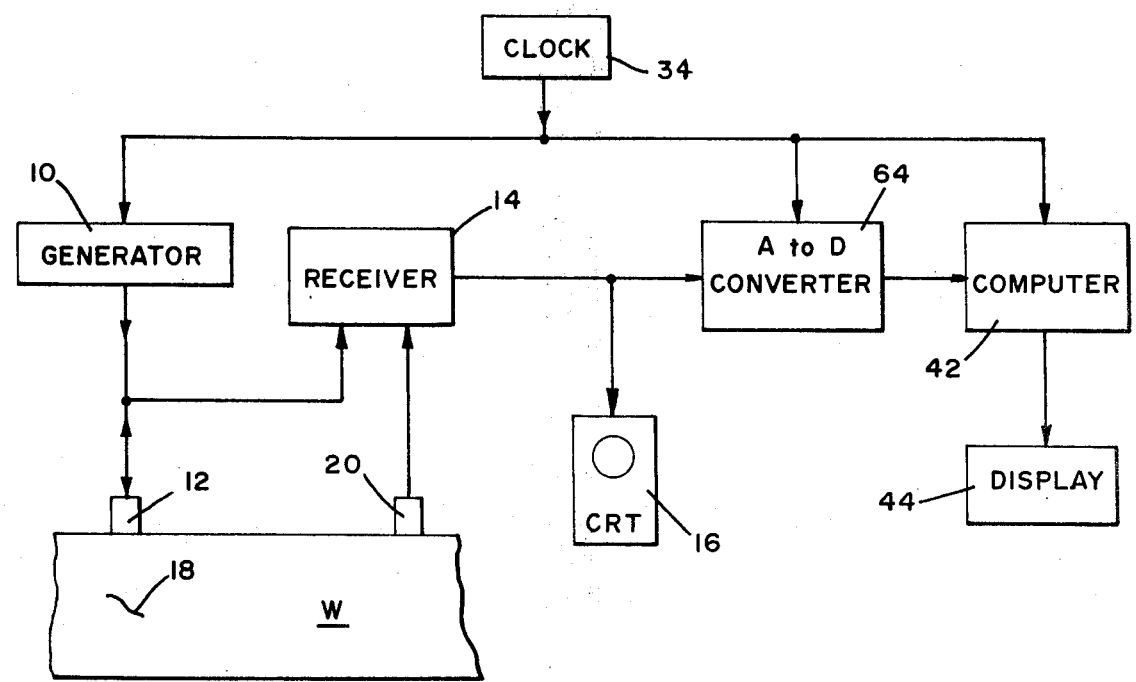

ULTRASONIC TEST METHOD AND APPARATUS UTILIZING SCATTERED SIGNALS

BRIEF SUMMARY OF THE INVENTION

This invention relates to testing of materials and more specifically concerns the testing of materials by ultrasonic energy using the pulse-echo technique.

The use of ultrasonic energy for testing a workpiece for internal defects such as flaws, cracks etc. is well established. Generally, a search pulse in the ultrasonic frequency range, typically 1 to 25 MHz, is transmitted from the surface of the workpiece into the interior thereof and an acoustic discontinuity, such as a flaw or crack, when intercepted by the search pulse causes a reflection which is transmitted back to the workpiece surface and is manifest as an echo signal. The echo signal, after conversion to an electrical signal, can be evaluated by well-known techniques, most commonly providing a two-dimensional analog display on a cathode ray tube. Based on experience and by the use of standardized calibration blocks, an operator can render a judgment as to the size and location of the defect in the workpiece. By manipulating the ultrasonic probe along the workpiece surface, the operator may be able also to some extent render a judgment as to the orientation of the defect. To a large measure, the evaluation technique depends upon the skill of the operator who must undergo training and maintain his skill.

When the search pulse intercepts an acoustic discontinuity a back reflected echo signal and a scattered reflected echo signal are transmitted toward the entrant surface of the workpiece. Under certain circumstances, when the angle of incidence of the search pulse at any portion of the acoustic discontinuity is less than the critical angle, the search pulse undergoes mode conversion at the acoustic discontinuity whereby, in addition to the back reflected echo signal and the reflected scattered echo signal, an additional mode-converted scattered echo signal is reflected toward the workpiece entrant surface. These three echo signals, the back reflected echo signal and the two scattered echo signals can be evaluated by known means to determine the size and location of a defect in the workpiece.

In view of the difficulty of establishing more precisely the nature of a defect and to distinguish between defects which provide substantially similar echo signals, yet differ in their physical characteristic, there has been a search for means to extract more information from the returned echo signal. One such technique is shown in U.S. Pat. No. 3,359,753 issued to Otto R. Gericke, "Ultrasonic Spectroscope" dated November 10, 1970. The patent discloses the use of a frequency spectrum analyzer for subjecting a selected echo signal to a frequency analysis. It has been found, however, that this method does not overcome, in many instances, the problem stated heretofore, specifically extracting from the return signal all of the available information concerning the physical characteristic of a defect.

In pending application for U.S. Letters Pat. Ser. No. 519,612, filed Oct. 31, 1974, now abandoned, entitled "Ultrasonic Test Method and Apparatus" there is disclosed a method of ultrasonic defect evaluation using digital computing means or the like for providing phase spectrum analysis of the reflected echo signal. The present invention reveals an improved arrangement utilizing digital computer means for providing a frequency amplitude spectrum and a frequency phase spectrum analysis of the back reflected echo signal and of the two scattered echo signals. The six resultant signals are further processed for determining more accurately to the extent possible the size, type, and orientation of defects in the workpiece.

A principal object of this invention is, therefore, the provision of an improved arrangement for evaluating defects using the ultrasonic pulse-echo test method.

A further important object of this invention is the provision of an ultrasonic test method having means for receiving a back reflected signal, a scattered signal and a mode converted scattered signal and analyzing these signals for more accurately determining the size, orientation and type of a defect in a workpiece.

Another object of this invention is the provision of an ultrasonic test method and arrangement for subjecting echo signals reflected from a defect to frequency and/or phase spectra analysis and a display of such analysis of the echo signals.

A still further object of this invention is the provision of means for subjecting spectra analysis responsive signals derived in an ultrasonic pulse-echo apparatus to additional transforms.

Another important object of the invention is the provision of means for combining the spectra analysis signals with other transform analysis signals.

Further and still other objects of this invention will be more clearly apparent by reference to the following description when taken in conjunction with the accompanying drawings.

DESCRIPTION OF THE DRAWINGS

FIG. 3 is an elevational view of an alternative embodiment of a portion of the diagram per FIG. 1;

FIG. 4 is a plan view of an array of received transducers useful for receiving the scattered echo signals reflected from an acoustic discontinuity in the workpiece;

FIG. 5 is a plan view of an alternative embodiment of the array of receive transducers per FIG. 4, and FIG. 6 is a schematic electrical block diagram of a further alternative embodiment of the circuit per FIG. 1.

DETAILED DESCRIPTION OF THE INVENTION

Figure 1:
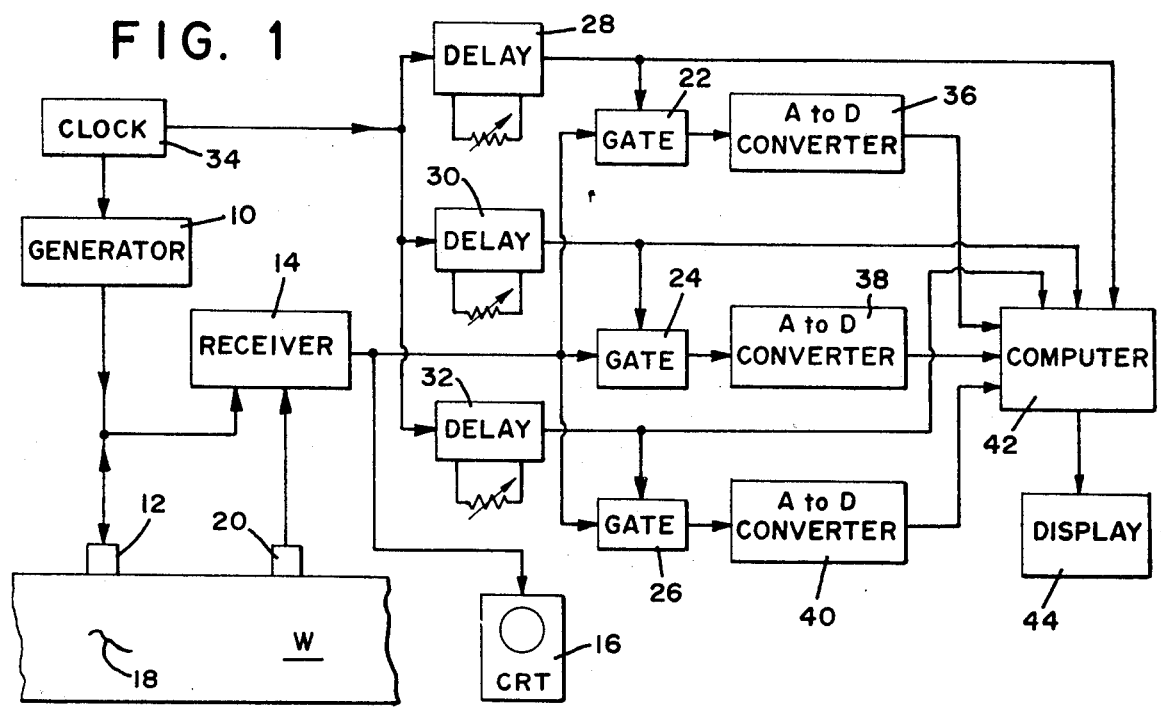
FIG. 1 is a schematic electrical block diagram of a preferred embodiment illustrating the broad principle of the invention.

Referring now to the figures, in FIG. 1, there is shown a pulse generator 10 which responsive to signals from a clock 34 cyclically applies to an electroacoustic transmit-receive transducer probe 12 of known construction an electrical signal in the ultrasonic frequency range. The transducer converts the applied signal to an acoustic signal and transmits the acoustic signal as a longitudinal wave search pulse into the workpiece W. A brief time interval thereafter the transducer probe 12 receives a back reflected longitudinal wave echo signal arising from a flaw, crack or other acoustic discontinuity 18 disposed in the workpiece. Such signal is converted by the transducer probe 12 into an electrical signal and transmitted to a first input channel of receiver 14. The receiver, in turn is coupled to a cathode ray tube 16 to provide an analog display of the amplitude of the echo signal as a function of elapsed time.

In addition to the reflected echo signal, two further signals are reflected from the acoustic discontinuity 18 toward an electroacoustic receive transducer 20 coupled to the entrant surface of the workpiece. Due to the scattered effect at the discontinuity, there will be a scattered longitudinal wave and also a mode-converted shear wave, the latter traveling at a lower speed than the longitudinal wave. The two scattered signals, which are received later in time than the back reflected signal, are converted to electrical signals by the receive transducer 20 and conducted to a second input channel of receiver 14. These signals are provided also to the cathode ray tube 16. The two separate input channels of the receiver 14 serve to isolate the transducer 20 from the pulse generator 10. A receive transducer 20 capable of receiving longitudinal mode acoustic signals is also capable of receiving scattered shear wave signals and converting the received scattered shear mode signal into electrical signals. A mode converted scattered shear wave signal from defect 18 received by transducer 20 in a direction non-perpendicular to the face of the transducer 20 comprises two vector components. A first component parallel to the face of transducer 20 and a second component normal to the face of transducer 20. The component normal to the face of the transducer 20 will cause an electrical signal which is conducted to receiver 14 for further processing. Thus, a longitudinal mode receive transducer 20 will respond to the scattered longitudinal mode wave signal and sense also a signal produced by the shear mode wave signal. Alternatively, an angle probe can be substituted for transducer 20 to receive the scattered shear mode wave signal.

Moreover, the output signals from the receiver 14 are provided to respective gate circuits 22, 24 and 26. A delay circuit 28, 30 and 32 is associated with a respective gate circuit. The clock 34 which triggers the pulse generator 10 also provides an input clock pulse to each delay circuit 28, 30 and 32. Each delay circuit, typically a monostable multivibrator, is adjustable for causing a respective output signal to be conducted to a selected gate circuit at the time when a respective echo responsive output signal is anticipated. Thus, the delay circuit 28 provides a signal to gate 22 for opening this gate shortly before the reflected longitudinal signal is received by the transmit receive transducer probe 12. Delay circuit 30 provides a signal to gate 24 for passing the scattered longitudinal output signal from receiver 14, and delay unit 32 provides a signal to open the gate 26 for passing the slower traveling scattered shear wave output signal. The signal from a respective delay circuit causes the normally closed associated gate to be opened for a time duration sufficient for the echo responsive signal to pass therethrough and thereafter causes the gate to resume its closed state. When gate 22 is open the reflected longitudinal echo signal received by the transducer probe 12 and converted to an electrical signal is conducted from receiver 14 via gate 22 to the analog-to-digital converter 36 which provides a sequence of digital values responsive to the instantaneous signal amplitude. In a similar manner, when gate 24 is open, the scattered longitudinal wave echo responsive electrical signal is conducted from receiver 14 via gate 24 to the analog-to-digital converter 38. Likewise, when gate 26 is open, the scattered transverse wave echo responsive electrical signal is conducted from receiver 14 via gate 26 to the analog-to-digital converter 40. Each delay circuit provides a signal to computer 42 for ensuring that the signal received by the computer from the respective analog-to-digital converters is recognized and processed in the computer as the proper wave responsive signal.

The analog-to-digital converters 36, 38 and 40 convert the analog signal manifest at the output of the receiver 14 into digital form signals compatible with a digital computer 42.

The output of the digital computer 42 is displayed on a display 44, for instance, a plotter, a printer, a television screen or the like.

Figure 2:
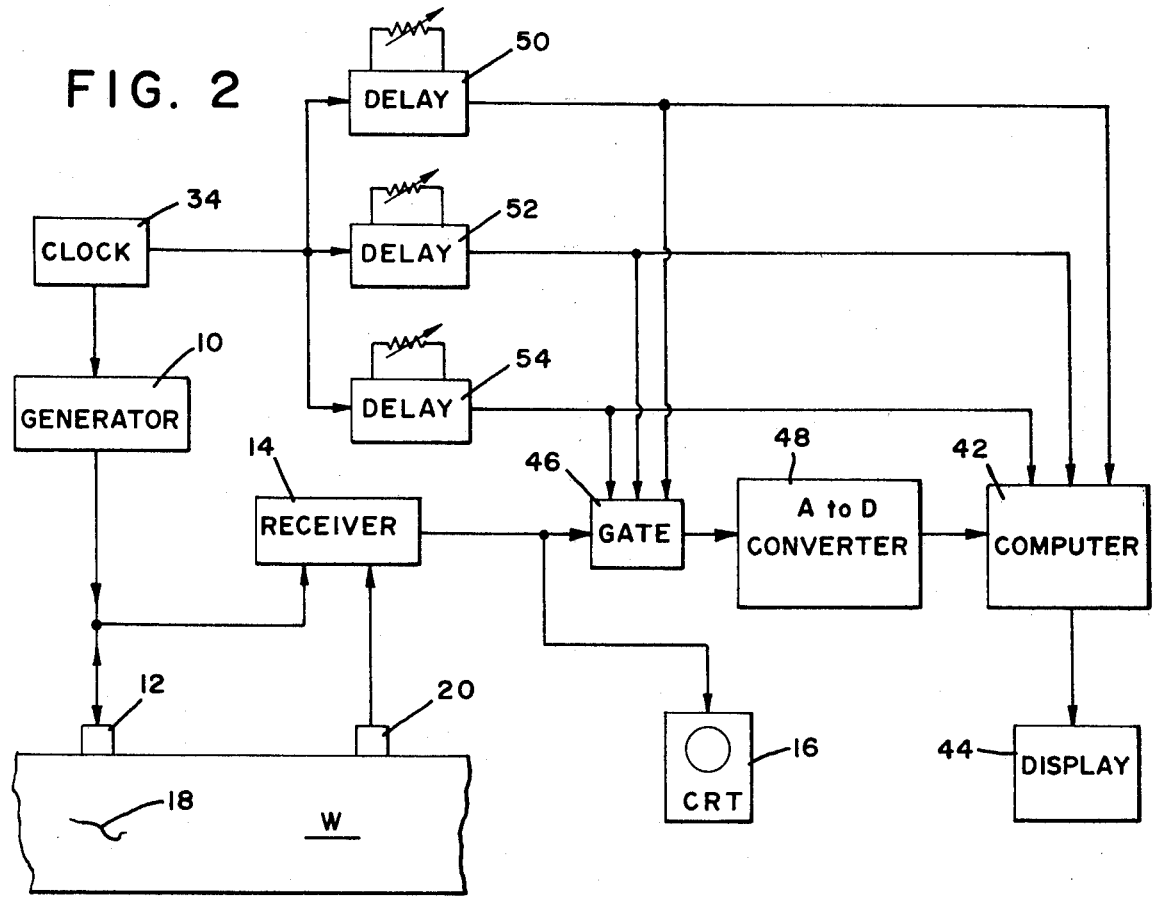
FIG. 2 is a schematic electrical block diagram of an alternative embodiment of the circuit per FIG. 1.

FIG. 2 depicts an alternative embodiment of the electrical circuit. All three echo responsive electrical signals are conducted from the receiver 14 through a single gate 46 to an analog-to-digital converter 48. Three delay circuits 50, 52 and 54 are adjusted as described in conjunction with the delay circuits 28, 30 and 32 in FIG. 1. The gate circuit 46 is opened for causing the desired signals to pass sequentially to the analog-to-digital converter 48. The analog-to-digital converter 48 digitalizes the analog signal. The delay circuits provide signals to the computer 42 as described above.

While in the foregoing description the transducer probe 12 is coupled to the workpiece W for transmitting and receiving longitudinal wave acoustic signals, it will be apparent that the method and apparatus described will perform in the identical manner when a transducer 56 is coupled to the workpiece W by a wedge 58 which converts the generated longitudinal acoustic signal to a shear wave acoustic search signal, see FIG. 3. The transmit-receive electroacoustic transducer 56 receives the defect responsive back reflected signal and laterally displaced receive transducer 20, as above, receives a mode converted scattered longitudinal wave echo signal and a slower traveling scattered shear wave echo signal. The back reflected shear wave signal is converted on account of the wedge 58 to a longitudinal wave acoustic signal which is then received by the transducer 56.

The angle at which each of the two scattered signals are reflected from an acoustic discontinuity in the workpiece differs. While in FIGS. 1 and 2 the broad principle of the invention is shown, in actual practice a single receive transducer 20 will be of limited utility. An improvement is obtained when the single electroacoustic receive transducer 20 is replaced by an array of receive transducers. FIG. 4 depicts a two-dimensional transducer array 60 coupled to the entrant surface of the workpiece. Each receive transducer 20' of the array 60 is electrically connected in sequence via an analog-to-digital converter to the digital computer. After the echo signals from all of the transducers 20' in the array have been digitized and stored in computer 42, the computer selects the optimum one or ones of the receive transducers 20' programmed for receiving the scattered longitudinal wave and scattered shear mode echo signals reflected from the defect. It will be apparent that depending upon the angle and depth within the workpiece at which the defect 18 is disposed a different probe 20' will receive the maximum amplitude reflected echo signal. The computer 42 is programmed to select the transducer 20' receiving the largest amplitude reflected scattered signal and to process the signal received from that transducer as described below. The scattered longitudinal echo signal and the scattered shear echo signal may be reflected from the defect 18 at different angles. In that instance, the transducer 20' which receives the largest amplitude longitudinal mode scattered echo signal does not receive the largest amplitude shear mode scattered echo signal. The computer selects both signals exhibiting maximum amplitude. The two signals thus selected and the back reflected signal are processed as will be described below. In an alternative embodiment, the computer is programmed to process a spatial distribution instead of the maximum values.

In an alternative embodiment, see FIG. 5, a circular array 62 of receive transducers 20'' is used to receive the scattered signals. It will be apparent that in a further modification, the center transducer 12' is the transmit-receive transducer, that is transducer 12' transmits the search pulse into the workpiece W and receives the back reflected echo signal whereas the surrounding receive transducers 20'' receive the scattered echo signals.

In FIG. 6, a further alternative embodiment of the circuit per FIG. 1 is shown. In this embodiment all of the video signals are provided to an analog-to-digital converter 64. The analog to digital converter 64 provides a first signal indicative of the instantaneous amplitude of the video signal and a second signal indicative of the time after "main bang" at which the measurement is made. The analog to digital converter 64 and the computer 42 each receive clock pulses from clock 34 for providing synchronization of the analog-to-digital converter 64 and the computer 42. The gates previously described in the present embodiment are programmed into the digital computer 42. Hence, signals received by the computer 42 during a time interval corresponding to the receipt of the respective echo at the transducer 12 or 20 are stored in and processed by the computer 42 as described below.

The output from the analog-to-digital converter provides a signal $x(t)$, in the form of discrete digital values. In the present embodiment, the computer is programmed by well-known techniques to compute for a given $x(t)$, the values of the Fourier transform:

$$S(f) = \int_{-\infty}^{+\infty} x(t)e^{-j2\pi ft} dt$$

for producing simultaneously the frequency spectrum and the phase spectrum of the signal $x(t)$; see paragraph 5–6 in "Analysis of Linear Systems" by D. K. Cheng, Addison-Wesley Publishing Company, Reading, Mass. (1959).

The output of the computer can be programmed to show on the display unit 44 a graph of the amplitude versus frequency of the Fourier transform of the signal $x(t)$ (amplitude spectrum) and a graph of the phase angle versus frequency of the Fourier transform of the signal $x(t)$ (phase spectrum). The resultant graphs, an amplitude and phase spectrum analysis for each of the three received echo signals are compared in the computer to stored graphs. Each defect in the workpiece results in a unique "signature" of six graphs. Typically, the ratio of the peak amplitudes of the amplitude spectra, the center frequency, the frequency difference between successive peaks, etc. of each amplitude spectra are regarded as figures of merit. Likewise, the frequency at which the phase angle of the transform signal is zero degrees, the rate of change of phase angle per unit frequency, the frequency difference of successive zero degree frequencies or peak phase angle frequencies, etc. are considered figures of merit of the phase spectra curve. The above stated list of figures of merit is not to be considered an all inclusive list but is intended, rather, to be suggestive of various characteristics of the Fourier transform which are useful for pattern recognition.

The computer 42 rapidly compares the graph and/or "figures of merit" of the graphs with stored data to determine the size, type, nature and location of a defect. It will be apparent that not all of the graphs need be used, selected one or ones of the graphs may provide the necessary information for defining a defect. For example, using only the amplitude spectra or only the phase spectra or combinations of the two types of spectra can provide a unique "signature" of a defect. The methods of computer pattern recognition to make a best match of the graphs are well-known.

It will be apparent that while the foregoing description describes Fourier transformation of the signal $x(t)$, other mathematical transformations may be performed such as Laplace, Hilbert, Hadamard, etc. which may then be evaluated in the digital computer.

While in the foregoing description only the amplitude spectrum and phase spectrum were analyzed for characterizing a defect, it will be apparent that the computer can be programmed for processing and analyzing a two-dimensional spatial transform arising from each transducer in the transducer array.

The various spectrum signals may also be mathematically combined with other transform signals to obtain, for instance, the product of spectrum signals. Hence, the resultant signals provide a unique signature of the characteristic of the defect within the workpiece which can then be compared with signatures stored in a computer memory. As used in this specification the term "mathematically combined" shall comprise, without limitation, such operations as multiplication, division, absolute value, square, square root, addition, substraction, or convolution of one, selected ones or all of the transform signals.

Aside from using a digital computer for providing graphical data of the amplitude and phase spectrum of the transformed signal other means known in the art may be used.

What is claimed is:

1. The method of evaluating a defect in a workpiece by the ultrasonic pulse echo principle comprising:
    transmitting an ultrasonic search pulse signal into a workpiece; sensing the back reflected acoustic wave signal arising from the search pulse signal intercepting an acoustic discontinuity in the workpiece;
    sensing further the scattered longitudinal wave and the scattered shear wave acoustic signal responsive to scattering of the transmitted pulse signal by said discontinuity;
    converting said sensed wave signals to respective electrical signals, and
    subjecting said electrical signals to transform analysis for providing an output signal indicative of the characteristics of said discontinuity.

2. The method of evaluating a defect in a workpiece as set forth in claim 1, said search pulse signal being a longitudinal sound wave.

3. The method of evaluating a defect in a workpiece as set forth in claim 1, said search pulse signal being a shear sound wave.

4. The method of evaluating a defect in a workpiece as set forth in claim 1, said transform analysis being frequency amplitude spectrum analysis.

5. The method of evaluating a defect in a workpiece as set forth in claim 1, said transform analysis being frequency phase spectrum analysis.

6. The method of evaluating a defect in a workpiece as set forth in claim 1, said transform analysis being frequency amplitude spectrum and frequency phase spectrum analysis.

7. The method of evaluating a defect in a workpiece as set forth in claim 1, said electrical signals comprising discrete digital values, and feeding said values to a digital computer programmed to provide said transform analysis of said fed digital values.

8. A pulse-echo ultrasonic defect test apparatus comprising:
 first transducer means coupled to a workpiece for transmitting an ultrasonic search pulse signal into the workpiece and for receiving a back reflected acoustic wave signal arising from an acoustic dicontinuity in the workpiece
 second transducer means coupled to the workpiece for receiving a scattered longitudinal wave acoustic signal and a scattered shear wave acoustic signal responsive to scattering of the transmitted pulse signal by said discontinuity, means coupled to said first and said second transducer means for providing a first electrical output signal responsive to said back reflected acoustic wave signal, a second electrical output signal responsive to said scattered longitudinal wave acoustic signal and a third electrical output signal responsive to said scattered shear wave acoustic signal, and
 signal evaluation means coupled for receiving said first, second, and third output signals for subjecting said first, second, and third output signals to transform analysis for providing a further output signal indicative of the characteristics of said discontinuity.

9. A pulse-echo ultrasonic defect test apparatus as set forth in claim 8, said signal evaluation means comprising computing means.

10. A pulse-echo ultrasonic test apparatus as set forth in claim 9, said computing means comprising a digital computer programmed for providing said transform analysis of said first, second, and third output signals.

11. A pulse-echo ultrasonic defect test apparatus as set forth in claim 8, said second transducer means comprising an array of transducers.

12. A pulse-echo ultrasonic defect test apparatus as set forth in claim 8, said evaluation means comprising digital computing means programmed for providing frequency amplitude and frequency phase spectra transform analysis of said first, second, third output signals.

13. A pulse-echo ultrasonic defect test apparatus as set forth in claim 9, and means coupled in circuit with said means coupled to said first and said second transducer means and said computing means for digitizing said first, second, and third output signals and feeding said first, second, and third output signals as discrete digital values to said computing means.

14. A pulse-echo ultrasonic defect test apparatus as set forth in claim 8, said evaluation means comprising digital computing means programmed for providing frequency amplitude spectra transform analysis of said first, second, and third output signals.

15. A pulse-echo ultrasonic defect test apparatus as set forth in claim 8, said evaluation means comprising digital computing means programmed for providing frequency phase spectra transform analysis of said first, second, and third output signals.

* * * * *